United States Patent
Bond et al.

(10) Patent No.: US 10,821,033 B2
(45) Date of Patent: Nov. 3, 2020

(54) COMPOSITION FOR THIN WALLED MOLDED PARTS

(71) Applicant: Edgewell Personal Care Brands, LLC., Chesterfield, MO (US)

(72) Inventors: Timothy Bond, Felton, TX (US); Patrick Gorton, Clifton Park, NY (US)

(73) Assignee: EDGEWELL PERSONAL CARE BRANDS, LLC, Chesterfield, MO (US)

( * ) Notice: Subject to any disclaimer, the term of this patent is extended or adjusted under 35 U.S.C. 154(b) by 586 days.

(21) Appl. No.: 15/606,221

(22) Filed: May 26, 2017

(65) Prior Publication Data

US 2017/0342236 A1    Nov. 30, 2017

Related U.S. Application Data

(60) Provisional application No. 62/341,769, filed on May 26, 2016.

(51) Int. Cl.
| | |
|---|---|
| A61F 13/28 | (2006.01) |
| A61F 13/26 | (2006.01) |
| C08K 3/34 | (2006.01) |
| C08K 5/20 | (2006.01) |
| C08K 9/02 | (2006.01) |
| A61L 15/18 | (2006.01) |
| A61F 13/20 | (2006.01) |
| C08K 3/22 | (2006.01) |

(52) U.S. Cl.
CPC ............ *A61F 13/28* (2013.01); *A61F 13/266* (2013.01); *A61F 13/2077* (2013.01); *A61F 13/2082* (2013.01); *A61L 15/18* (2013.01); *C08K 3/34* (2013.01); *C08K 5/20* (2013.01); *C08K 9/02* (2013.01); *C08K 2003/2241* (2013.01)

(58) Field of Classification Search
CPC .................................................. A61F 13/26–28
USPC ....................................................... 604/11–18
See application file for complete search history.

(56) References Cited

U.S. PATENT DOCUMENTS

| | | | |
|---|---|---|---|
| 5,986,000 A * | 11/1999 | Williams ................ | A61F 13/26 428/35.7 |
| 6,730,057 B2 | 5/2004 | Zhao et al. | |
| 7,226,436 B2 | 1/2007 | Gorham et al. | |
| 7,887,525 B2 | 2/2011 | Gorham et al. | |
| 8,070,710 B2 | 12/2011 | Dougherty, Jr. | |
| 8,551,034 B2 | 10/2013 | Dougherty, Jr. | |
| 2003/0040695 A1 | 2/2003 | Zhao et al. | |

(Continued)

*Primary Examiner* — Susan S Su

(57) ABSTRACT

A polymer composition comprising an organic polymer and a mica containing effect pigment, e.g., a pearlescent pigment comprising mica, well suited for producing molded articles, in particular, for molding articles comprising thin sections and or delicate features, such as a hollow interior defined by a thin wall or structural features susceptible to tear or other damage and the like, is provided as are a method for preparing molded articles comprising the polymer composition and articles comprising the polymer composition, including, for example, an article used to deliver a medical or personal care component such as a tampon applicator, and a method for preparing molded articles comprising the polymer composition. Optionally, articles of the present disclosure have a varying translucency or opacity about a dimension of the article.

12 Claims, 2 Drawing Sheets

(56) References Cited

U.S. PATENT DOCUMENTS

| | | | | |
|---|---|---|---|---|
| 2005/0070645 A1* | 3/2005 | Williams | ............... | A61F 13/26 524/132 |
| 2008/0167597 A1* | 7/2008 | Dougherty | ............. | C08L 23/06 604/12 |
| 2010/0198133 A1* | 8/2010 | Dougherty, Jr. | .... | A61F 13/2082 604/15 |
| 2011/0190685 A1* | 8/2011 | Arora | ...................... | A61F 13/26 604/14 |
| 2011/0240064 A1* | 10/2011 | Wales | ..................... | C09D 5/14 134/26 |
| 2011/0272860 A1* | 11/2011 | Walia | ..................... | C08L 23/10 264/328.17 |
| 2011/0319837 A1* | 12/2011 | Uehara | ................ | A61L 29/049 604/264 |
| 2015/0065942 A1* | 3/2015 | De Soto-Burt | ..... | A61F 13/2077 604/15 |
| 2017/0246042 A1* | 8/2017 | Ferrer | ................ | A61F 13/2077 |

* cited by examiner

COMPOSITION FOR THIN WALLED MOLDED PARTS

CROSS-REFERENCE TO RELATED APPLICATIONS

This application claims priority to U.S. Provisional Patent Application Ser. No. 62/341,769, filed May 26, 2016, the entirety of which are incorporated by reference herein.

BACKGROUND

A polymer composition comprising an organic polymer and a mica containing effect pigment, e.g., a pearlescent pigment comprising mica, well suited for producing molded articles, in particular, for molding articles comprising thin sections and or delicate features, such as a hollow interior defined by a thin wall or structural features susceptible to tear or other damage and the like, is provided as are a method for preparing molded articles comprising the polymer composition and articles comprising the polymer composition, including, for example, an article used to deliver a medical or personal care component, e.g., in one particular embodiment a tampon applicator, and a method for preparing molded articles comprising the polymer composition.

Polymer compositions are routinely molded into articles and parts of articles in common daily use. Such polymer compositions must provide the article with desired physical features, e.g., the desired degree of physical strength, stiffness or flexibility, transparency or opacity, etc., the desired aesthetic features, e.g., color, surface quality, other visual effects etc., and must be capable of producing an article with the desired size and shape, e.g., it must be able to form a final article with the desired thickness and design features which may include sharp angles, a degree of curvature, finely defined surfaces or appendages and the like.

Numerous applications require a product that possesses both highly functional properties in conjunction with highly aesthetic properties. This is especially true with consumer products, where the consumer is not only concerned with how well the particular product functions, but also how the product looks and feels. For example, many personal care of home care items that contact skin or other sensitive surfaces areas, often need to be soft, flexible, and/or lubricious in order to avoid discomfort, scratching, abrasion etc.

U.S. Pat. No. 8,551,034 discloses a lubricious polymeric composition comprising a polymer and one or more lubricants, and a method for making an article from the lubricious polymeric composition. Articles formed from the lubricious polymeric composition possess enhanced softness, flexibility and lubricity. Useful lubricants include fatty acid amides such as erucamide, oleamide, stearamide, stearyl erucamide, bis-erucamide, metallic stearate, ethylene bis stearamide, ethylene bis oleamide, etc., fatty acid glycerol esters, fatty acid salts, ethylene methyl acrylate copolymer, polytetrafluoroethylene, long chain hydroxyamines, alkane sulfonate salts, silanes, siloxanes and the like. Excellent results were obtained when fatty acid lubricants such as erucamide, stearamides and the like were employed.

U.S. Pat. No. 8,551,034 also discloses the use of pigments, including pearlescent pigments, in the composition, in concentrations of from 0.01 wt. % to 5 wt. %, preferably 0.2 wt. % to 2 wt. %, and more preferably 0.5 wt. % to 1.2 wt. % based on the total weight of the polymeric composition. The only teaching related to useful pearlescent pigment concentrations is found in polymeric compositions comprising about 98 wt. % to about 99 wt. % LDPE, about 0.6 wt. % mica (pearlescent pigment), about 0.5 wt. % titanium dioxide, about 0.25 wt. % erucamide, and less than about 0.01 wt. % colorant, which was also exemplified in the production of a tampon applicator barrel; and another polymeric composition comprising about 92 wt. % to about 93 wt. HDPE, about 5 wt. % LDPE, about 0.9 wt. % mica (pearlescent pigment), about 0.75 wt. % titanium dioxide, about 0.37 wt. % erucamide, and less than about 0.01 wt. % colorant, which was also exemplified in a tampon applicator plunger.

U.S. Pat. No. 7,226,436 discloses a multi-layered tampon applicator wherein at least one of the 'inner' layers is modified for improved visual/aesthetic properties, improved surface characteristics, and/or improved perception of insertion comfort. To provide optical enhancements, one of the layers may be a coating composition wherein one or more optical components are added to the resin and/or wax to impart aesthetic properties. Such components may include, e.g., mica, $TiO_2$-coated mica, iron oxide coated mica, bismuth oxychloride, holographic material, pearlescence material, reflective material, glitter, metallic effect pigment, interference pigment, liquid crystal effect material, or any combinations thereof. Preferred optical components are mica, $TiO_2$-coated mica, iron oxide coated mica and bismuth oxychloride. The use of $TiO_2$-coated mica having a particle size of about 2 microns to about 150 microns at 1 wt. % to about 60 wt. %, and $TiO_2$-coated mica having a particle size of about 2 microns to about 10 microns at about 2 wt. % to about 20 wt. %, and more preferably about 5 wt. % to about 15 wt. % in the coating is disclosed.

U.S. Pat. No. 9,192,522 discloses a tampon applicator assembly having an applicator barrel with an insertion tip and may be provided with a tapered insertion tip. A shaped pledget can be housed in the applicator barrel, which provides support to the petals. The pledget has a withdrawal element 51 such as one or more strings. The strings can be knotted, crimped, and/or the withdrawal element can be at least partially braided. For example, a tampon assembly comprising a barrel region having a plastic tubular wall having a plurality of discrete petals, separated from each other by a plurality of cuts extending along the barrel region that form a break of material through said tubular wall, that define a tapered shaped insertion tip region, and a tapered pledget having an end region that has been compressed to form a tapered insertion tip contacting and supporting at least the base regions of the petals. In one embodiment the barrel is formed from polyethylene, e.g., low-density polyethylene (LDPE). In another embodiment the barrel is from LDPE and a thermoplastic elastomer (TPE). The TPE may be a block co-polymer comprising styrene, butadiene or isoprene and styrene or other TPEs such as polyurethane elastomers and others.

U.S. Pat. No. 8,337,378 discloses a tampon applicator comprising a plunger and a barrel having a wall forming a tube with a center axis therethrough and with a hollow interior volume, which barrel comprises four distinct sections, namely a finger grip section, a reverse taper section, a main body section, and a tapered insertion tip section, wherein the reverse taper section is tapered towards the fingergrip section, and the main body section is tapered in an opposite direction towards the insertion tip section. A maximum diameter is formed where the reverse taper section and main body section meet on the barrel and provides a sensory indicator to the user to alert the user when the applicator has been inserted to the proper depth.

Various tampon applicator and tampon barrel architectures capable of being molded from polymer compositions are known, some examples of which can be found in U.S. D 515,212; U.S. D 572,362; U.S. D 579,113; U.S. D 612,940; U.S. D 492033; and U.S. D 511832.

Many polymer compositions capable of providing functional and aesthetic properties desired for certain products are not sufficiently compatible with some of the molding processes used in their production. For example, many polymer compositions, known to produce products with certain optical properties, such as those comprising pearlescent mica pigments, can generate an unacceptable amount of products that are torn, ruptured or otherwise damaged during certain molding processes, especially those which generate high stress on the polymer during processing. This is especially problematic when producing articles with very thin sections or certain details such as the petals of the tampon applicator described above.

It was found that reducing the amount the amount of mica typically present in such polymer molding compositions will allow one to prepare translucent or pearlescent articles, with aesthetic properties such as soft feel, flexibility, and/or lubricity that are desirable for many items, including, e.g., personal care items, without generating excessive waste due to scrap produced during molding, even when using high stress molding methods.

SUMMARY

One embodiment of the invention provides a polymer composition for preparing a molded article, also called a polymer molding composition, comprising, based on the total weight of the polymer composition:

from about 95 to about 99.8% of an organic polymer, from about 0.05 to 0.5%, e.g., about 0.1 to about 0.5% or 0.15 to about 0.35 or 0.4% of a pearlescent pigment comprising mica, from about 0.002 to about 0.1%, e.g., about 0.005 to about 0.07%, about 0.007 to about 0.05, of a colorant other than a pearlescent pigment comprising mica, from about 0.05 to about 1.0% of a lubricant comprising a fatty acid amide, and from 0 to 4.8%, e.g., about 0.05 to about 4.8% other additives.

The pearlescent pigment comprising mica typically comprises a mica particle coated with one or more layers, wherein at least one layer comprises titanium dioxide.

Colorants other than the pearlescent pigment comprising mica can be one of a wide variety of pigments or dyes, but in many embodiments pigments are preferred, including white pigments, including e.g., inorganic white pigments such as titanium dioxide, effects pigments, such as other pearlescent pigments, black pigments including composite back pigments and carbon black, and organic and inorganic pigments of various colors other than black or white. Combinations of more than one such colorant are often used.

The other additives, when present, typically comprise one or more additive selected from the group consisting of plasticizers, compatibilizers, flow modifiers, antioxidants, antistatic agents, fillers, reinforcements, surfactants, light/UV stabilizers, thermal stabilizers, impact modifiers, processing aids, other lubricants, flame retardants, biocides, antiozonants, blowing agents and anti-foaming agents, however, any polymer additive commonly used in the art may be present in the polymer molding composition.

The organic polymer may comprise a thermoplastic, elastomeric or thermoset polymer, and generally comprises a thermoplastic and/or an elastomeric polymer, and often comprises a thermoplastic polymer. In many embodiments the organic polymer comprises, for example, a polyolefin polymer or copolymer, polyester, polyamide, polystyrene, polyvinyl chloride, polyacrylate, polymethacrylate, polyvinyl alcohol, polylactic acid, or a moldable starch, for example, polyethylene, linear low density polyethylene, low density polyethylene, high density polyethylene, near low density polyethylene, polypropylene, copolymers comprised of ethylene, styrene, isoprene or butadiene monomers, and in some embodiments the organic polymer comprises low density polyethylene, high density polyethylene or a mixture of low density polyethylene and high density polyethylene. More than one organic polymer may be present in any composition of the present invention.

The lubricant comprises a fatty acid amide, such as erucamide, oleamide, stearamide, stearyl erucamide, bis-erucamide, ethylene bis stearamide, ethylene bis oleamide, etc., for example, erucamide, oleamide, stearamide, stearyl erucamide or bis-erucamide. In some embodiments other lubricants are also be present, such as one or more of the lubricants found, for example, in U.S. Pat. No. 8,551,034 cited above.

Another broad embodiment provides a process for preparing the above polymer compositions. While one can prepare the composition by mixing together the various polymers, pigments, lubricants etc., in the desired amounts according to any standard processing technique, it is often desirable to first prepare a color concentrate (also referred to as a carrier) comprising the pearlescent pigment comprising mica, colorant other than pearlescent pigments comprising mica, the lubricant and other optional additives and a smaller amount of polymer than is present in the inventive polymer composition, and then compounding the concentrate with a base polymer.

For example, one embodiment provides a process for producing the polymer composition above, i.e., polymer molding composition, which process comprises compounding a mixture comprising from about 1 to about 10 wt %, e.g., from about 2 to about 6 wt %, of a color concentrate and from 90 to 99 wt %, e.g., 94 to 98 wt %, of a base polymer wherein the base polymer comprises an organic polymer and the color concentrate comprises, based on the total weight of the polymer composition:

from about 50 to about 95% of an organic polymer, from about 0.5 to about 10%, e.g., about 4 to about 8% of a pearlescent pigment comprising mica, from about 0.02 to about 1.3%, e.g., about 0.3 to about 1.0 of a colorant other than a pearlescent pigment comprising mica from about 0.5 to about 10% e.g., about 1.5 to about 3.0% of a lubricant comprising a fatty acid amide and from 0 to about 40% other additives.

One must select the appropriate let down ratio, i.e., weight percent (wt. %) of color concentrate compounded into the base polymer in order to prepare a polymer molding composition according to the present invention. For example, using 10 wt. % of a color concentrate comprising 10 wt. % of a pearlescent pigment comprising mica results in a polymer composition of comprising 1 wt. % of the pearlescent pigment comprising mica, which is well outside the ranges of the present invention, whereas the same concentrate at a 2 wt. % let down results in a composition having 0.2 wt. % of the pearlescent pigment, which is within the range of the inventive composition.

One particular embodiment of the invention provides the above color concentrate.

The organic polymer of the color concentrate and the base polymer comprise one or more of the polymers cited above for the polymer molding composition. The polymer or mixture of polymers in the color concentrate may be the same as, or different from, the polymer or mixture of polymers of the base polymer.

The pearlescent pigment comprising mica, colorant other than a pearlescent pigment comprising mica, lubricant comprising a fatty acid amide, and other additives of the color concentrate are those described above for the molding composition.

The base polymer may also comprise one or more of these components, for example pearlescent pigment, colorants, lubricants, processing aids, stabilizers etc., but the base polymer would comprise the pearlescent pigment comprising mica or colorant other than a pearlescent pigment comprising mica at a much lower level than found in the concentrate, if at all. In many embodiments the base polymer does not comprise either the pearlescent pigment or other colorant. The base polymer may also comprise a lubricant, which may or may not be the same lubricant of the color concentrate, in some embodiments the base polymer does not comprise a lubricant.

Compounding refers to a process wherein an intimate mixture of components is created. In the present case, this may be any known method of compounding, including high shear mixing, blending the components, typically in a molten state, at elevated temperature, extrusion, etc. In one particular process, the compounding step is integrated with the process of molding an article, for example, a mixture of the color concentrate and base polymer may be added to an extruder, extruded to prepare an intimate mixture of the components and then directly injected into a mold. In other embodiments, the polymer molding composition is prepared separately from the molding step, e.g., it may be extruded and pelletized, Another broad embodiment of the invention provides a molded article comprising the polymer composition above, i.e., polymer molding composition, a process for preparing such an article, and an improved process for reducing scrap when molding articles under high stress conditions. In many embodiments the article comprises certain optical effects, e.g., pearlescence, translucency etc. In particular embodiments the article is variably translucent, meaning that the degree of translucence varies in different sections of the article. The article may also vary in color, e.g., the hue, depth, or lightness of the color may vary indifferent sections of the article.

The article of the invention may comprise one thickness or various thicknesses. Many embodiments provide a molded article wherein at least a portion of the article has a thickness ranging from about 0.002 mm to about 2.0 mm, e.g., about 0.05 mm to about 1 mm, or about 0.1 mm to about 0.9 mm. Some embodiments provide an article wherein the entire article comprising the polymer composition of the invention is 2 mm or less than 2 mm thick.

In particular embodiments the molded article comprises a hollow interior volume typically accessible through one or more openings, which hollow interior volume is at least partially defined by one or more walls comprising the polymer molding composition. For example, the article may comprise a generally tubular void or cup shaped void defined by at least one curved wall comprising the polymer molding composition, which wall has one or more thicknesses in of from about 0.002 mm to about 2.0 mm, from about 0.05 mm to about 1 mm, or from about 0.1 mm to about 0.9 mm.

One particular embodiment provides a device, or part of a device, which device is a delivery apparatus for a medical, personal care, home care or veterinary item, for example, a device comprising a barrel and a plunger wherein the barrel comprises an interior hollow volume from which the medical, personal care, home care or veterinary item is delivered, wherein the barrel and/or plunger comprises the polymer molding composition of the invention. In one particular exemplary embodiment of the invention the device is a tampon applicator, but other devices comprising the present polymer composition are also prepared from the present polymer composition.

The present invention is particularly useful in molding an article comprising structural features associated with causing rupture (i.e., fracturing and/or splitting) of the article during molding. For example, a device comprising at least two sections having structural features different than the other, and wherein at least one section comprises one or more features associated with causing rupture of the article during molding, such as tapering to a thickness of less than 1 mm, a slit, an angle of 90 degrees or less especially in a section less than 2 mm or less than 1 mm thick, a narrow joint between two wider sections, or a section that is placed under higher physical stress during processing than other sections of the article. For example, in one embodiment the polymer molding composition is used to prepare the barrel of a tampon applicator comprising a hollow interior volume defined by a curved wall and two ends, wherein the barrel tapers toward one end having an opening, which end may also comprise petals, e.g., sections separated by slits in the wall, typically curved in a manner to narrow or temporarily close the barrel, which will open under pressure to allow for exit of an absorbent pledget.

The articles of the invention may be formed by many known molding processes including, e.g., injection molding or compression molding the present polymer molding composition.

One embodiment provides a compression molding process comprising at least partially filling an open mold cavity with the polymer composition of the invention, which in many embodiments is formed according to the letdown process above, and then inserting a second mold member into the polymer composition in the open mold to define a space between the open mold cavity and the second mold member and to force the polymer composition to fill said space to form an article of the invention. The polymer composition may be molten or softened to a point where it can be forced to fill the space between the open mold cavity and the second mold element either before or during the molding process, and either or both of the mold cavity or second mold element may be heated at a temperature to melt or soften the polymer composition.

Forming an article by molding the polymer composition of the invention using the above injection molding or compression molding processes has been found to greatly reduce the amount of scrap from torn, ruptured or otherwise malformed articles.

DETAILED DESCRIPTION

Figure 1:
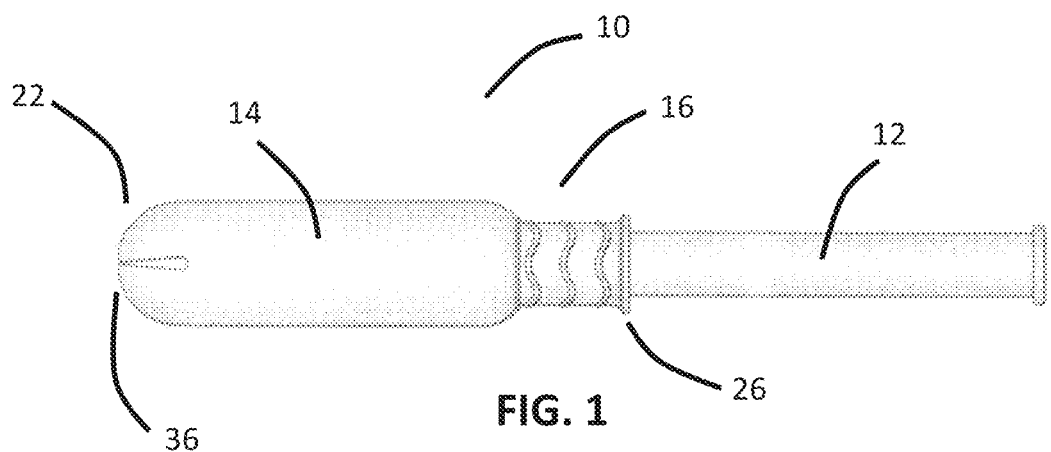
FIG. 1 is a diagrammatic view of a tampon applicator according to the present disclosure.

The polymer composition of the present invention can be used to mold articles having a variety of functional and aesthetic properties and can be used to prepare articles useful in applications with particular requirements, such as personal care applications, where a soft or lubricious feel is a necessity and where a consistency in overall appearance contributes greatly to consumer confidence. In applications such as these, certain properties that may be considered ancillary or aesthetic in other applications assume a more primary importance as it relates to the present disclosure. The present polymer composition readily provides such articles with excellent structural, color, and other optical properties, but also may be used to form articles with high degrees of softness, flexibility and/or lubricity.

The polymer composition of the invention comprises one or more organic polymers typically selected from common synthetic polymers or naturally occurring materials such as a polyolefin polymer or copolymer, polyester, polyamide, polystyrene, polyvinyl chloride, polyacrylate, polymethacrylate, polyvinyl alcohol, polylactic acid or moldable starch. The polymers may be thermoplastic, elastomeric or thermoset polymers, but typically comprise a thermoplastic and/or an elastomeric polymer. Most often the polymer will comprise a thermoplastic polymer or a blend of a thermoplastic and elastomeric polymer.

For example, the polymer often comprises a polyethylene, low density polyethylene, high density polyethylene, linear low density polyethylene, polypropylene, or a copolymer comprised of ethylene, styrene, isoprene or butadiene monomers. In many embodiments the organic polymer comprises low density polyethylene, high density polyethylene or a mixture of low density polyethylene and high density polyethylene.

In some embodiments, the organic polymer comprises a blend of a polyethylene, e.g., low-density polyethylene and a thermoplastic elastomer. For example, the organic polymer may comprise a blend of about 50 wt. % to about 90 wt. %, e.g., about 80 wt. %, low-density polyethylene and about 50 wt. % to about 10 wt. %, e.g., about 20 wt. %, thermoplastic elastomer, based on a total weight of the composition. One useful thermoplastic elastomer is a tri-block (terpolymer), having an A-B-A configuration of monomers, in which monomer B is not the same as monomer A. Typically the blocks comprise styrene, butadiene, or isoprene monomers. Other classes of useful thermoplastic elastomers include, for example, thermoplastic polyurethane elastomers.

A variety of additives are common in polymer compositions included processing aids, stabilizers, colorants, etc. . . . . Any suitable additive common in the field may also be used in the present composition, including for example, plasticizers, compatibilizers, flow modifiers, antioxidants, antistatic agents, fillers, reinforcements, surfactants, light/UV stabilizers, thermal stabilizers, impact modifiers, processing aids, other lubricants, flame retardants, biocides, antiozonants, blowing agents, anti-foaming agents and the like.

In order to possess or maintain the proper softness and/or lubricity needed in many of the articles of the invention, the composition contains at least 0.05 wt. % of a lubricant, which lubricant comprises a fatty acid amide. Typically, the lubricant comprises erucamide, oleamide, stearamide, stearyl erucamide, bis-erucamide, ethylene bis stearamide, ethylene bis oleamide, etc., for example, erucamide, oleamide, stearamide, stearyl erucamide or bis-erucamide.

Other optional lubricants may also be present in addition to the fatty amide, for example, calcium stearate, glycerol monostearate, magnesium stearate, calcium stearate, zinc stearate, aluminum di-stearate, fatty acid glycerol esters, calcium soaps of montanic acids, triglyceryl esters of hydroxy saturated fatty acids, ethylene methyl acrylate copolymer, polytetrafluoroethylene, micronized PTFE, mineral oil, C14-18 alkyl di(2-hydroxyethylamine), sodium alkane sulfonates, dimethicone and other polydimethyl siloxanes, t-butyldiphenylchlorosilane, other polar aromatic and aliphatic silanes such as chloromethyldimethylchlorosilane, epoxylated soybean oil, oxidized polyethylene wax, K-Y jelly and/or glycerol.

One skilled in the art will be able to adjust the lubricity of an article formed from the present polymer molding composition by varying the total amount of lubricant present in the composition.

The composition comprises a pearlescent pigment comprising mica which serves to provide a variety or optical properties to the composition, and colorants, e.g., pigments and dyes, for example organic and inorganic pigments other than the pearlescent pigment comprising mica. The pearlescent pigment comprising mica typically comprises a mica particle, such as a mica platelet or flake, which is coated with one or more layers of other materials, e.g., metal oxides, silicas, etc. . . .

The pearlescent pigments themselves are particles, often in a generally platelet or flake form, which are typically not of a uniform shape. U.S. Pat. No. 7,226,436 discloses TiO2-coated mica having a particle size of about 2 microns to about 150 microns, and TiO2-coated mica having a particle size of about 2 microns to about 10 microns. Pearlescent pigments are also known that are defined by having a diameter and a defined thickness in the range of plus or minus 10%, of the average thickness. For example, the particles may be flakes having a thickness of from 20 to 2000 nm, e.g., from 100 to 350 nm and a diameter of about 1-60 microns, e.g., about 5-40 microns.

In many embodiments of the invention, the pearlescent pigment comprising mica comprises a mica, particle, flake or platelet coated by one or more layers, wherein at least one of these coating layers comprises titanium dioxide. Generally, the pigment particle fits within the one of the above dimension ranges. A variety of such pigments are commercially available, including, e.g., CI Pigment White 20, also known as PW 20.

In addition to providing the composition with a nacreous sheen, the pearlescent pigment also has the ability to affect the opacity of the composition and contribute to varying degrees of translucency. One particular optical effect that can be imparted to an article produced using the polymer composition of the invention is variable translucence. That is, an article can be formed from the composition where a portion of the article is more translucent than another portion of the article. As used herein. the term "same color" means colors having the same hue but which can differ in intensity. such as lightness and darkness. As used herein. the term "visually perceptible" to a consumer is meant that a human viewer can visually discern a difference with the unaided eye (excepting standard corrective lenses adapted to compensate for nearsightedness. farsightedness. or astigmatism. or other corrected vision) in lighting at least equal to the illumination of a standard one-hundred-watt incandescent white light at a distance of 0.25 meter. As used herein. the term "translucent" means that a consumer can visually perceive what is on the opposite side of the transparent object or thing. The term translucent also includes transparent regions. As used herein. the term "opaque" means that a consumer cannot visually perceive what is on the opposite side of the opaque object or thing.

In some embodiments, translucency is a gradient along a dimension of the article (i.e. such as the length, width, or a radial dimension). In some embodiments, the insertion tip region has a translucency of up to 100% (i.e. is not opaque), is up to 75%, is up to 50%, is up to 25%, is up to 10% translucent, where such translucent portion is at least at a single dimensional location along the insertion tip. For instance, in some embodiments, the highest translucency portion of the insertion tip is at the tip end. In other embodiments, the insertion tip has a gradient of translucency/opacity along the length of the insertion tip. In some such embodiments, the insertion tip end (also referred to as forward end) 36 has the greatest translucency, while the end of the insertion tip region adjacent the barrel region has the lowest translucency of the tip region (or said differently, the highest opacity).

In other embodiments, the barrel region has a translucency of up to 100%, up to 75%, up to 50%, up to 25%, up to 10%, or having 0% translucency. In some embodiments, the barrel region has a gradient of translucency/opacity along the length of the barrel region. In some such embodiments the gradient favors translucency on either or both of the extremes of the barrel region (i.e. adjacent (a) the insertion tip, or (b) depending on the embodiment, adjacent the reverse taper region or the grip region).

In other embodiments having a reverse taper region (as with, for example, at least FIGS. 5 and 5A), the reverse taper region has a translucency of up to 100%, up to 75%, up to 50%, up to 25%, up to 10%, or having 0% translucency. In some embodiments, the reverse taper region has a gradient of translucency/opacity along the length of the reverse taper region. In some such embodiments the gradient favors translucency on either or both of the extremes of the reverse region (i.e. adjacent (a) the barrel region, or (b) adjacent the grip region).

In other embodiments, the grip region has a translucency of up to 100%, up to 75%, up to 50%, up to 25%, up to 10%, or having 0% translucency. In some embodiments, the grip region has a gradient of translucency/opacity along the length of the grip region. In some such embodiments the gradient favors translucency on either or both of the extremes of the grip region (i.e. adjacent (a) the barrel region, or (b) at the distal end of the grip region).

In other embodiments, the plunger has a translucency of up to 100%, up to 75%, up to 50%, up to 25%, up to 10%, or having 0% translucency. In some embodiments, the plunger has a gradient of translucency/opacity along the length of the plunger. In some such embodiments the gradient favors translucency on either or both of the extremes of the plunger (i.e. (a) the plunger end engaging the pledget, or (b) the rearward end of the plunger opposite the pledget engaging end).

In some embodiments having a two-piece plunger (as in FIG. 5), either or both plungers have a translucency as described in the preceding paragraph. In further embodiments, the two plungers have a translucency (or opacity) that is different in an initial, disconnected state, and an in-use, connected state. In some such embodiments, the translucency or opacity is further distinct with regard to the connection region, particularly in the in-used, connected state.

Translucency (or opacity) can be influenced by the amount of mica containing pearlescent pigment used, the amount of other colorants present and the ratio of pearlescent pigment comprising mica to other colorant, etc. Other factors such as the organic polymer, the shape of the article, the thickness of the article or difference in the thicknesses of article comprising more than one thickness can play a role. It is also possible that the stress on various sections of the article, e.g., a section stressed by undue curvature, or the stresses experienced by the composition during the molding process may play a role in the relative amounts of translucence.

The present polymer composition comprises 0.5 wt % or less, of the pearlescent pigment comprising mica, e.g., less than 0.5 wt % such as 0.4 wt % or less, which is lower than the level typically encountered in other similar compositions, e.g., U.S. Pat. No. 8,551,034 or 7,226,436. Without being bound onto theory, it appears that it is this lower level of mica containing pearlescent pigment that allow one to prepare relatively thin articles using certain economically favorable but high stress molding techniques, such as forced compression molding, without excessive scrap.

The colorants other than the pearlescent pigment comprising mica can be almost any other colorant, such as dyes, inorganic pigments or organic pigments, provided that they are compatible with the polymer, processing technique, and end use. For example, certain colorants such as dyes may leach out of the polymer on storage or in use. Such colorants would be generally unsuitable in an article that contacts the skin or delivers a medical or personal care item. In certain embodiments the only mica containing pigment present in the polymer composition is the pearlescent pigment comprising mica.

Useful colorants include, e.g., white pigments and opacifiers, such as titanium dioxide and other inorganic white pigments. Black pigments including carbon blacks and composite blacks may be used as well as a wide variety of known yellow, orange, red, violet, green, blue, pink and other colored pigments and dyes. Surprisingly, it has been found that, without modulating such colorants, the opacity can be reduced, or said differently, the translucency increased.

Examples of organic pigments include azo, azomethine, methine, anthraquinone, phthalocyanine, perinone, perylene, diketopyrrolopyrrole, thioindigo, dioxazine, iminoisoindolinone, quinacridone, benzimidazolone, flavanthrone, indanthrone, anthrapyrimidine and quinophthalone pigments, or a mixture or solid solution thereof. Suitable inorganic pigments include, for example, metal oxides, mixed metal oxides, and metal sulfides. A small selection of specific pigments include ultramarine blue, cobalt blue, manganese blue, cobalt green, cerium sulfide, cadmium sulfide, cadmium sulfoselenides, zinc ferrite, bismuth vanadate, iron oxide, red iron oxide, orange iron oxide, white zinc sulfide, aluminum powder, bronze powder, phthalocyanine green, phthalocyanine blue, phthalocyanine red, diarylide yellow, quinacridone red, rhodamine red, lithol rubine red, napthol red, neozapon red, carbizole violet, barium sulfate and the like.

The selection of appropriate colorant is within the skill of the average practitioner. Often, more than one colorant is used to generate the desired color.

Some of the advantages of the present invention can be illustrated in a specific embodiment. For example, a tampon applicator of FIG. 1 comprises a barrel and a plunger. A pledget comprising an absorbent material is held within the barrel until ejection by the plunger. A softer applicator barrel is more comfortable and is a desirable feature of a tampon applicator in order to provide improved ease of insertion.

Consumers are interested in tampon applicators that are soft yet resilient (i.e. resist forces encountered when inserting into the body such that the product is insertable and doesn't merely collapse or deform thereby rendering insertion a failure or difficult), comfortable to insert, with a suitable ejection force. Translucency, to some degree, of a portion of the tampon applicator, if not multiple portions, is advantageous as it enables the consumer to see the absorbent product (i.e. a tampon pledget) within the applicator such that the consumer can see the pledget (or portions thereof such as the tip, the withdrawal element, etc. . . . ) and understand how it is being deployed (and afterwards, confirming it has been deployed as the applicator appears vacated). A softer applicator barrel is more comfortable and is a desirable feature of a tampon applicator in order to provide improved ease of insertion and a noticeable degree of lubricity is also often desired. Tampon manufacturers want applicators made of inexpensive, low-cost materials that are easy, rapid and inexpensive to manufacture at high volumes and tampons that can be assembled at high speeds with only minor modifications.

Presently, molding compositions used in the formation of plastic tampon applicators can deliver high quality articles, but some of these compositions are not fully compatible with certain economically advantageous manufacturing processes. Further complicating the manufacturing issues, many successful tampon applicator designs comprise features that are often difficult to form in high volume manufacturing processes. For example, the barrels of some tampon assemblies include a dome shaped end, FIG. 1, or a tapered end for comfort and ease of insertion, FIG. 2, that includes a number or plurality of shaped petals configured to open during ejection of the pledget. The petals are separated from each other by a plurality of cuts extending along the barrel region that form a break of material through said tubular wall that are visible in FIGS. 1 and 2, which cuts can create site where tearing during formation of the barrel.

The petals need to readily and smoothly open without undue resistance during ejection of the pledget from the barrel. The petals are thus preferably soft, highly flexible and thin-walled. FIG. 4A shows a schematic diagram of a tampon assembly of the invention, wherein the pledget has a tapered end that can support at least a part of the petals during insertion of the applicator assembly, which allows for thinner, softer, more flexible petals.

Figure 4:
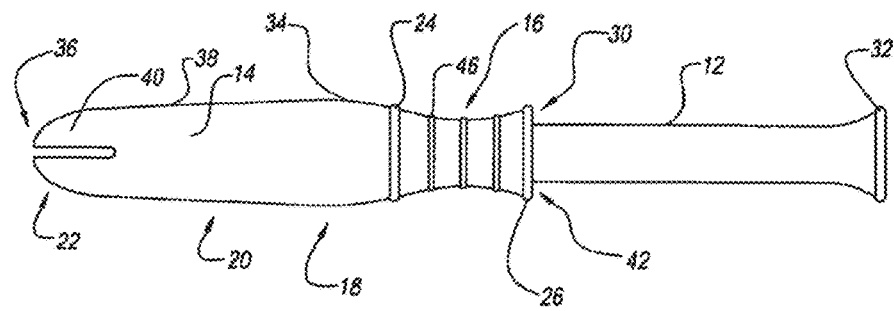
FIG. 4 is a diagrammatic view of a tampon applicator according to the present disclosure.
Figure 4A:
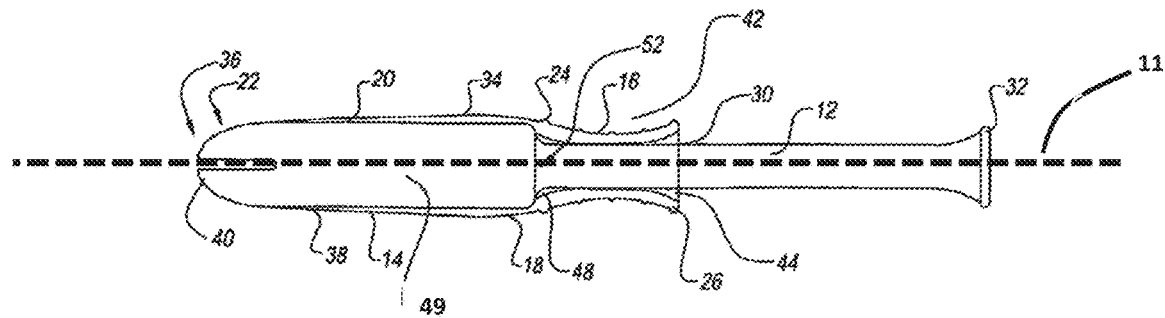
FIG. 4a is a diagrammatic sectional view of a tampon applicator according to the present disclosure.

FIGS. 4 and 4A illustrates a tampon applicator of the invention having a barrel and a plunger with a flared end, wherein the barrel has various widths and walls with various thicknesses, and comprises a grip region, a reverse taper region, a barrel region and an insertion tip region, wherein the insertion tip region is tapered, the main body section has a maximum diameter section that is sensually perceivable to a user to alert the user to the proper insertion depth of the applicator, and a reverse taper region towards the grip region.

Figure 5:
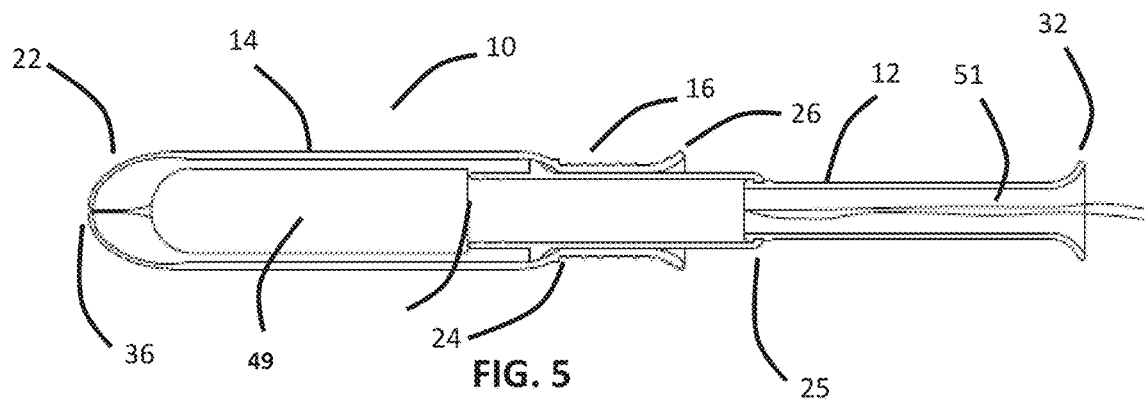
FIG. 5 is a diagrammatic sectional view of a tampon applicator according to the present disclosure.

FIG. 5 illustrates a tampon applicator having a two-piece plunger (i.e. a first plunger segment and a second plunger segment).

The manufacturer is thus faced with the task of efficiently and economically preparing soft, tubular, tapered, thin-walled, lubricious plastic parts with various widths and thicknesses, with soft, flexible, curved appendages that are formed buy cuts into a tube under a degree of stress due to the curvature of the walls. Preparing such parts using certain molding processes with compositions having commonly used levels of pearlescent pigments comprising mica, such as those used in the present invention, has led to an unacceptably high level of scrap due to barrel splitting due largely to the cuts into the barrel that form the petals, and/or the use of post-forming features onto the molded article by compression molding (i.e. forming a tapered or flared end of the grip region, and/or the plunger).

The use of the polymer molding composition of the invention in molding operations to form molded articles such as these tampon applicator barrels has been shown to provide high quality, smooth, soft, thin-walled, lubricious barrels with excellent aesthetic properties, while also reducing the amount of scrap due to, e.g., barrel splitting. In one example, tampon barrels comprising a tapered insertion tip with petals as described above were prepared by molding a polymer composition of the invention having between 0.15 wt. % and 0.33 wt % pearlescent mica containing pigment, which produced significantly less scrap than when the barrels were prepared using a similar molding composition comprising between 1 wt. % and 1.3 wt. % of the same pearlescent pigment.

The structural advantages of using the polymer composition of the invention molding other articles should be apparent to anyone skilled in the art.

Other advantageous results can also be realized. For example, the polymer composition of the invention can produce articles with various visual properties including high gloss, excellent color, pearlescence, translucency and variable translucency. In preparing the tampon barrels described above, for example, depending on the exact conditions and compositions used, barrels could be prepared with a high degree of variable translucency, such that barrels are very translucent in the tapered tip and petals and become deeper in color and less translucent in the regions further away from the tip. However, it is possible through minor variations in the polymer composition to produce a barrel with high gloss, consistent color, and a more moderate variance in translucency. It is also possible to produce barrels with high gloss and little or no translucency.

For example, a color concentrate comprising about 6.4 wt. % pigment white 20 (a pearlescent pigment comprising mica), about 0.9 wt. % of a mixture comprising titanium oxide and other colored pigments, about 2.8 wt. % of a mixture of erucamide and a bis stearamide in a low density polyethylene carrier was let down at 3.5% and 3.0% into a low density polyethylene base polymer and the barrels as described above were molded using the resulting polymer compositions. Barrels prepared from the 3.0% and 3.5% letdowns were both variably translucent, the barrel produced from the 3.0% letdown was highly translucent at the tip, whereas the barrel produced from the 3.5% letdown was more moderately translucent at the tip. These samples demonstrate a gradient effect of translucency to color over a portion of a molded article, such as over the length of the entire applicator barrel, a portion of the applicator barrel such as the insertion tip, the barrel region, the reverse taper region, the grip region, and/or the plunger, such as a first plunger segment, a second plunger segment, a portion of a plunger (or plunger segment), etc. . . . . In some embodiments, a translucency to color gradient can be further modified by varying the thickness (i.e. along the length) of the molded part.

Barrels can also be prepared from the color concentrate above at higher let down ratios, e.g., 5%, 6%, 7%, 8% and above 8% etc., but as the letdown ratio with this particular color concentrate increases past about 5%, a gradual increase is scrap becomes noticeable. In alternative embodiments, let down ratios of less than 2% are also possible.

As stated, the polymeric composition, i.e., the polymer molding composition, of the invention may be formed by any suitable method known in the art. For example, the polymeric composition can be formed by combining the proper amount of all the components in a twin-screw extruder, and then extrude the molten mixture which can then be cut to into pellets, but any high temperature and/or high shear method that produces an intimate mixture of the components can be used. However, as known in the art and as seen above, small changes in the polymer molding composition can cause noticeable changes in an article prepared therefrom, and greater control over the formation of the polymer molding composition can be obtained by letting down a color concentrate into a base polymer.

One embodiment of the invention thus provides a process for producing the polymer molding composition, which comprises compounding a mixture comprising from about 1 to about 10 wt. %, e.g., from about 2 to about 6 wt. %, of a color concentrate and from 90 to 99 wt. %, e.g., 94 to 98 wt. %, of a base polymer wherein the base polymer comprises an organic polymer and the color concentrate comprises, based on the total weight of the polymer composition:

from about 50 to about 95% of an organic polymer, from about 0.5 to about 10%, e.g., about 4 to about 8% of a pearlescent pigment comprising mica, from about 0.02 to about 1.3%, e.g., about 0.3 to about 1.0 of a colorant other than a pearlescent pigment comprising mica from about 0.5 to about 10% e.g., about 1.5 to about 3.0% of a lubricant comprising a fatty acid amide and from 0 to about 40% other additives.

Selecting the proper letdown ratio for a given color concentrate in order to prepare a polymer molding composition of the invention comprising the required components is within the purview of one skilled in the art, i.e., a poly composition comprising from about 0.05 to 0.5%, e.g., about 0.1 to about 0.5% or 0.15 to about 0.35 or 0.4% of a pearlescent pigment comprising mica, from about 0.002 to about 0.1%, e.g., about 0.005 to about 0.07%, about 0.007 to about 0.05, of a colorant other than a pearlescent pigment comprising mica, from about 0.05 to about 1.0% of a lubricant comprising a fatty acid amide, and other optional additives.

The color concentrate in the aforementioned example comprises about 6.4 wt. % pigment white 20 (a pearlescent pigment comprising mica), about 0.9 wt. % of a mixture comprising titanium oxide and other colored pigments, about 2.8 wt. % of a mixture of erucamide and a bis stearamide in a low density polyethylene carrier and can be let down at a ratio of 2 to 6%, or 2.5 to 6% into a suitable polymer to produce a polymer composition of the invention useful in preparing the. For this particular composition, the most desirable results in producing the tampon applicator barrel above were achieved at let down ratios of 2.5 to 5%, and in some cases excellent results were achieved at a letdown ratio of 3 to 4%. However, color composition with a different composition, e.g., a different ratio of pearlescent pigment to other colorant or the use of different pigments etc., may require a different letdown ratio for the best results.

Barrels were prepared in a variety of colors including green, lime green, orange, magenta, turquoise, and dark green using molding compositions prepared in a manner analogous to that above, but using different colorants. Other colors are within the scope of the present disclosure, including without limitation, shades of green, shades of blue, shades of red, shades of purple, shades of pink, shades of white, shades of orange, and shades of yellow.

A color composition comprising larger quantity of pearlescent pigment would likely require a lower letdown ratio and the use of a different base polymer affects what the optimum level of the various components should be.

Furthermore, other molded articles prepared according to the present invention, e.g., a bottle or other container, a delivery apparatus for an oral or other veterinary composition, a medical device etc., can have a different set of specific properties that are most desirable, and therefore best results would likely be provided using a different optimal concentration, within the limits of the present disclosure, of polymer molding composition components and color concentrate components, and different letdown ratios. However, optimizing the present invention in such a manner would be within the purview of one skilled in the art after reading the present specification.

Compounding the color concentrate with the base polymer can occur through any known method, e.g., extrusion, high shear mixing, using solid colorant or carrier composition, blending of a liquefied molten mixture of color concentrate and base polymer etc. It is also possible to lend a liquefied or molten color concentrate with a liquefied or molten base polymer. The compounding of the color concentrate with the base polymer can also be integrated with the molding process, for example, an extrusion step or other melt blending step can be integrated with injection molding. In one embodiment, a liquefied or molten color concentrate and a liquefied or molten base polymer are fed into an apparatus which mixes the components and feeds the result into a mold.

The actual molding process may also employ any known method, e.g., cast molding, injection molding, compression molding, other post-processing or post-forming means, etc. The tampon barrel exemplified above, for example, can be efficiently formed by injection molding. Another efficient and economical process for forming the barrel comprises partially filling an open mold with the polymer molding composition, frequently a molten composition, and compressing the composition with a second mold member.

Temperatures and pressures and exact processing conditions used in molding the articles of the invention will vary. In the preparation of the barrels exemplified above, post-processing pressures between 200 psi and 1,000 psi, and temperatures having an upper range between 225° F. and 300° F. were often employed. To manufacture such articles via injection molding, pressures between 11,000 psi and 14,000 psi were used, and temperatures between 380° F. and 425° F. were employed.

Despite the polymer composition's value in forming other articles, the particular embodiment comprising a tampon applicator, and specifically the barrel of a tampon applicator, can be used to demonstrate many advantages of the invention, and more will be said about it here.

Figure 2:
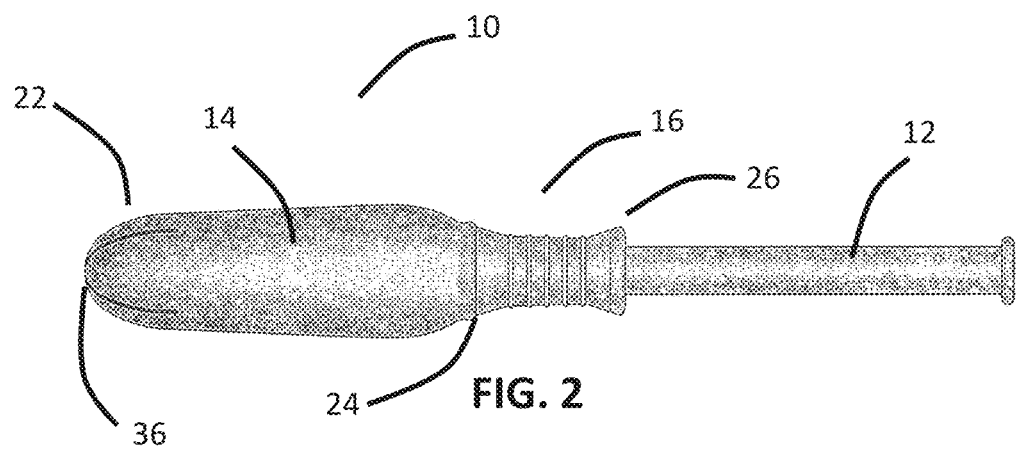
FIG. 2 is a diagrammatic view of a tampon applicator according to the present disclosure.
Figure 3:
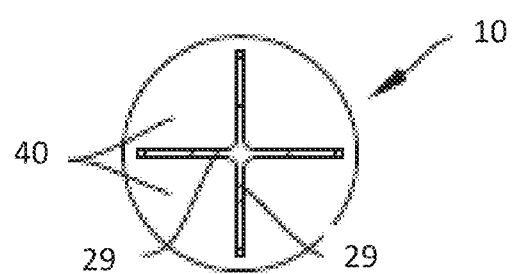
FIG. 3 is a diagrammatic view of a tampon applicator according to the present disclosure.

FIGS. 1 and 2 show tampon applicators of the invention comprising a barrel and a plunger that extends into the barrel at one end. The end opposite the plunger comprises the insertion tip and petals that open when pressed to allow the pledget to be ejected. FIG. 3 shows an end view of an insertion tip having 4 petals, Tampon applicators having 3 petals are also known, and applicators having more than 4 petals are easily envisaged (i.e. 5, 6, 7, and 8 petals). At least FIGS. 1, 2, and 4 show the slits or cuts 29 that define the petals. These cuts may vary in length depending on the desired length of the petal.

One embodiment of the invention provides a tampon applicator barrel comprising the polymer composition of the invention. In another embodiment, the barrel and/or the plunger comprise the polymer composition of the invention.

FIGS. 2, 4 and 4A also illustrates a tampon applicator of the invention wherein the barrel is tapered becoming more narrow at the insertion tip. In embodiments wherein the tampon applicator is variably translucent, the region near and/or comprising the insertion tip is typically more translucent than other portions of the applicator barrel, for example, the wider section of the barrel in embodiments having a tapered barrel region. In one embodiment of the invention, the thickness of the barrel wall is the same through the barrel, but in another embodiment, as shown in FIG. 4A, the barrel wall has multiple thicknesses, and in a particular embodiment the barrel wall, including the petals, is thinner at or toward the ejection tip than it is at the wider portion of the barrel.

One particular tampon applicator embodiment is illustrated in FIGS. 4 and 4A which includes a plunger 12 and a barrel 20. Barrel 20 is divided into four sections including a grip region 16, a reverse taper region 18, a barrel region 20, and an insertion tip region 22. As used throughout the present disclosure, the terms "section" and "region" are interchangeable. The term "main barrel section" is interchangeable with "barrel region", the term "finger grip section" is interchangeable with "grip region", the term "reverse taper section" is interchangeable with "reverse taper region", as are statements similar to these.

Grip region 16 is bound by a forward edge ridge 24 and a rearward edge ridge 26. Forward edge ridge 24 provides a firm grip surface during insertion of applicator 10 into the vaginal vault. Rearward edge ridge 26 provides a firm grip surface during expulsion of the pledget (not shown) and during removal of applicator 10 from the body. Forward and rearward edge ridges 24, 26 are about 6 mm to about 22 mm in diameter, e.g., about 11 mm to about 17 mm in diameter, and in one embodiment, about 14 mm.

A grip region 16 is formed between forward edge ridge 24 and rearward edge ridge 26. To ensure an adequate area to accept a user's finger or fingers, forward edge ridge 24 and rearward edge ridge 26 are spaced about 13 mm to about 40 mm apart, e.g., about 17 mm to about 21 mm apart, and in one embodiment about 19 mm. Grip region 16 may be concave, convex, flat, or any combinations thereof, typically region 16 is concave, which conforms to the contour of a user's finger. The maximum diameter of grip region 16 is preferably slightly less than the diameter of edge ridges 24, 26. Preferably, grip region 16 has a maximum to minimum diameter ratio of about 1.10 to about 1.75, with a more preferred ratio of about 1.25 to about 1.35.

Grip region 16 may also include one or more gripping structures to improve grippability of applicator 10, for example, one or more and preferably two or more, embossments, protuberances, slits, grooves, louvers, perforations, lances, abrasive medias, high wet coefficient of friction materials, pressure sensitive adhesives, or any combinations thereof. In addition, gripping structures 46 may be formed in any shape, including, for example, arc, circle, concave, cone, convex, diamond, line, oval, polygon, rectangle, rib, square, triangle, or any combinations thereof.

The maximum diameter 34 of applicator barrel 20 occurs at the forward end of reverse taper section 18. Reverse taper is meant to include a taper in the reverse direction, i.e. in a direction away from the insertion tip end 36 of applicator 10, but not necessarily the same dimensional taper as main body section 20. The diameter of reverse taper section 18 tapers down toward forward edge ridge 24, where the diameter is equal to or slightly less than the diameter of forward edge ridge 24. This taper may be linear or curvilinear.

Maximum diameter 34 of barrel 20 exerts a slightly greater pressure than the smaller diameter portions of the barrel 20 on the vaginal opening. Thus, the location of maximum diameter 34 along the length of barrel 20 is a critical aspect of this particular embodiment as it provides a sensually perceivable way of signaling or indicating to a user that applicator 10 has been inserted to the correct depth. The location of maximum diameter 34 on barrel 20 is about 32 mm to about 54 mm in the axial direction of barrel 20 from forward end 36 of insertion tip 22. Preferably maximum diameter 34 is located about 40 mm to about 50 mm, and more preferably about 44 mm in the axial direction of barrel 20 from forward end 36 of insertion tip 22.

Barrel region 14 is joined to reverse taper region 18 where maximum diameter 34 of barrel 20 is located. Barrel region 14 tapers toward insertion tip section 22 in either a linear or curvilinear fashion so that its smallest diameter occurs where barrel region 14 meets insertion tip region 22. The ratio of maximum diameter 34 to the diameter at the forward end 38 of barrel region 14 is about 1.1 to about 1.5, and more preferably about 1.2 to about 13. This tapering of barrel region 14 facilitates insertion comfort by gradually parting the vulva-vaginal channel over a longer length than that of only insertion tip region 22.

Insertion tip region 22 begins where there is a substantial change in the curvature of the forward portion of the barrel that is where the pledget 49 enclosing petals 40 are formed. In applicator designs where no petals are used, insertion tip region 22 is the forward edge of the barrel region 20 of barrel 14. The preferred insertion tip region 22 is the petal type with a curvature that approximates an elliptical or hyperbolic curve. Preferably, insertion tip 22 has about 2 to about 12 petals, and more preferably about 3 to about 8 petals. The ratio of the maximum diameter of insertion tip section 22, which occurs at the plane where its rearward edge meets forward end 38 of main body section 20, to the total axial length of the insertion tip section along a center axis 11 of applicator 10, is about 0.9 to about 1.8, and more preferably about 1.1 to about 1.3.

It should be understood that while tampon applicator barrel 14 of FIGS. 4 and 4a are depicted as having four sections, namely a grip region, a reverse taper region, a barrel region, and an insertion tip region, the tampon applicator barrel can include a reverse taper region and at least one additional section selected from a grip region, a barrel region, an insertion tip region, or any combinations thereof.

The interior wall of barrel 14 that houses the pledget may have the same basic sidewall shape as its exterior wall. However, molding such a complicated interior wall requires a complex manufacturing process. Alternately, the interior wall can be practically straight walled (a slight taper may be required for tooling release) while the exterior wall has the sectional shapes discussed before, thus simplifying the molding process.

Referring to FIGS. 2 and 3, barrel 14 has a finger grip end 42. Plunger 12 telescopically fits into the finger grip end 42 of barrel 14. Plunger 12 has a diameter slightly smaller than the smallest diameter of grip region 16 so that plunger 12 telescopically fits throughout the interior of barrel 14. In one embodiment of the present plunger 12 has a diameter about 4 mm to about 18 mm, e.g., plunger 12 has a diameter about 5 mm to about 9 mm, e.g., about 7 mm.

Plunger 12 has a first flare 32 at its distal end and a second flare or retaining structure 48 at its opposite barrel end 52. Grip region 16 has a plunger receiving end 30. Plunger receiving end 30 of grip region 16 has a chamber 44 to receive first flare 32 of plunger 12 during pledget expulsion. This permits shortening the length of the section of plunger 12 that protrudes from barrel 14 since all of the protruded length is available for the telescopic action. This in turns results in a more ergonomic applicator.

First flare 32 has a maximum diameter about 6 mm to about 22 mm. Preferably the maximum diameter is about 12 mm to about 16 mm, with about 13 mm being the most preferred maximum diameter, in order to provide a secure area for a user's fingertip during pledget expulsion. The rearward end of first flare 32 may be flat, concave, or convex. Preferably, it is concave to provide a secure area for the fingertip.

Second flare 48 has a maximum diameter about 5 mm to about 20 mm. Preferably the maximum diameter is about 11 mm to about 14 mm, with about 13 mm being the most preferred maximum diameter, in order to prevent separation from barrel 14.

Although it might be implied that the cross-sectional shape of plunger 12 and barrel 14 is circular, due to the use of the term 'diameter', it should be understood that the cross-sectional shape can be non-circular, such as oval or polygonal. Furthermore, the cross-sectional shape can vary along the length of both plunger 12 and barrel 14. For example, a circular plunger with a polygonal finger grip and an oval main body may be formed.

The polymer molding composition of the invention can be used in the preparation of either plunger 12 and/or barrel 14.

FIGS. 4 and 4A are schematic representations of a tampon assembly comprising a plunger 12, a barrel 20 that tapers and becomes more narrow at or towards the insertion tip region, and a pledget 49 comprising a withdrawal cord 51, which pledget 49 in this case is also tapered and supports the petals 40.

Plunger 16 is useable to expel pledget 49 from barrel 14. Plunger 16 is slideably disposed in barrel 14 at second end 22. Pledget 49 is expelled through first end 20 through the movement of plunger 16 in the direction of arrow 32. As plunger 16 moves in the direction of arrow 32, the plunger can urge pledget 49 into petals 26 until the petals open along slits 29 and the pledget is expelled from barrel 14 through insertion tip 24.

Insertion tip region 22 is, preferably, tapered or elliptical in shape. Specifically, insertion tip region has a linear or non-linear taper from the insertion tip end 36 to the opposite end adjacent the barrel region.

The taper of insertion tip 22 is defined as a ratio of the maximum radial dimension of insertion tip 22, divided by length of the insertion tip region 22. In one embodiment of the present disclosure, insertion tip 22 has a taper ratio of more than about 0.3 to less than 1.0. In another embodiment, insertion tip 22 has a taper ratio of more than about 0.4 to less than about 0.8. In yet another embodiment, insertion tip 22 has a taper ratio of about 0.4 to about 0.5. An insertion tip 22 that tapers gently towards the insertion tip end 36 is preferred for insertion ease, insertion comfort.

Pledget 49 is shaped to support insertion tip 22.

Pledget 49 supports a portion of inner surface area of the applicator barrel 14. The tip end of the pledget 49, most preferably, has a shape closely matching a shape of insertion tip 22 to provide proper support for petals 26. The taper ratio of the pledget tip end, preferably, matches the shape of insertion tip 22.

Advantageously, shaped pledget 13 prevents forces on insertion tip 22 applied during insertion of barrel region 14 into the body from collapsing petals 40 inward towards the pledget. Further, shaped pledget 49 enables the petals 40 to be made thinner to decrease the expulsion force while still mitigating the collapse or deflection of petals 40. In one embodiment of the present disclosure the petals 40 have a thickness between about 0.005 inches (0.127 mm) to about 0.03 inches (0.762 mm), and any range there between. In a preferred embodiment, the petals have a thickness between about 0.006 inches (0.1 mm) to about 0.013 inches (0.330 mm). In another preferred embodiment, the petals have a thickness between about 0.008 (0.203 mm) inches to about 0.011 inches (0.279 mm).

Some specific embodiments of the invention include, for example, an applicator comprising the polymer composition of the invention, a tampon applicator comprising said barrel, or a tampon assembly comprising said barrel, which barrel comprises a wall forming a tube with a center axis 11 therethrough and with a hollow interior volume, the tube having a first barrel end and a second barrel end opposite the first barrel end that is a free end, the first barrel end and the second barrel end form a length there between that corresponds to the length of the center axis 11, the tube increasing in diameter along the length of the tube from a first diameter to a second diameter that forms a main body section, and decreasing in diameter along the length of the tube from the second diameter to a third diameter that forms a reverse taper section, wherein the center axis 11 is substantially straight throughout the extant of the tube, wherein the second diameter is a maximum diameter of the tube. In many embodiments the first diameter of the barrel is connected to an insertion tip section. Typically the diameter of the tube decreases in diameter along the length of the tube from the first diameter to the first barrel end in the insertion tip section and the insertion tip section generally has a plurality of petals formed by slits or cuts in the tube.

In some embodiments the third diameter of the barrel connects directly to a finger grip section, wherein the finger grip section has a forward edge ridge adjacent the reverse taper section, wherein the finger grip section has a rearward edge ridge at the second barrel end, and wherein the forward edge ridge and the rearward edge ridge has a finger accepting region there between, and in some embodiments the finger grip section has a length from the third diameter to a fourth diameter, and wherein the tube decreases in diameter from the third diameter to the fourth diameter.

In some embodiments the tube increases in diameter along the length of the tube from the fourth diameter to a fifth diameter and in some embodiments the fifth diameter is at the second barrel end, wherein the second barrel end has an opening into the interior volume for receipt of a plunger.

In the tampon applicator 10 or tampon assembly the plunger 12 typically has a first plunger end 52 and a second plunger end 32, wherein the first plunger end 52 is within the interior volume and the second plunger end 32 has a shape that is complimentary to the shape of the grip region 16 between the fourth diameter and the fifth diameter. In the tampon assembly comprising the barrel above, the barrel has an interior wall that houses a pledget opposite an exterior wall and the pledget 49 is shaped to have a tapered end that supports at least a portion of the petals 40.

In particular embodiments of the above barrel, tampon applicator or tampon assembly, the barrel increases in translucency at the insertion tip region.

The features found in the figures and specific embodiments discussed above represent specific aspects of particular embodiments of articles prepared using the polymer molding composition of the invention, but the molded articles of the invention are certainly not limited to only these aspects or embodiments.

What is claimed is:

1. A polymer molding composition, comprising, based on the total weight of the polymer composition:
   from about 95 to about 99.8 wt. % of an organic polymer,
   from about 0.15 to 0.33 wt. %, of a pearlescent pigment comprising mica,
   from about 0.002 to about 0.1 wt. % of a colorant other than a pearlescent pigment comprising mica,
   from about 0.05 to about 1.0 wt. % of a lubricant comprising a fatty acid amide and from 0 to about 4.8 wt. % other additives.

2. The polymer molding composition according to claim 1 wherein the pearlescent pigment comprising mica comprises a mica particle coated with one or more layers, wherein at least one layer comprises titanium dioxide.

3. The polymer molding composition according to claim 1 or 2 wherein the lubricant comprises erucamide, oleamide, stearamide, stearyl erucamide or bis-erucamide.

4. The polymer molding composition according to claim 2 comprising from about 0.005 to about 0.07 wt. % of a colorant other than a pearlescent pigment comprising mica.

5. The polymer molding composition according to claim 1, comprising from about 0.05 to about 4.8 wt. % other additives comprising one or more additive selected from the group consisting of plasticizers, compatibilizers, flow modifiers, antioxidants, antistatic agents, fillers, reinforcements, surfactants, light/UV stabilizers, thermal stabilizers, impact modifiers, processing aids, other lubricants, flame retardants, biocides, antiozonants, blowing agents and anti-foaming agents.

6. The polymer molding composition according to claim 1, wherein the organic polymer comprises one or more polyolefin polymer or copolymer, polyester, polyamide, polystyrene, polyvinyl chloride, polyacrylate, polymethacrylate, polyvinyl alcohol, polylactic acid, and/or moldable starch.

7. The polymer molding composition according to claim 6 wherein the organic polymer comprises polyethylene, low density polyethylene, high density polyethylene, near low density polyethylene, polypropylene, copolymers comprised of ethylene, styrene, isoprene or butadiene monomers.

8. A tampon applicator assembly, comprising, based on the total weight of a polymer composition:
   from about 95 to about 99.8 wt, % of an organic polymer,
   from about 0.05 to 0.4 wt. %, of a pearlescent pigment comprising mica,
   from about 0.002 to about 0.1 wt. % of a colorant other than a pearlescent pigment comprising mica,
   from about 0.05 to about 1.0 wt, % of a lubricant comprising a fatty acid amide and from 0 to about 4.8 wt. % other additives;
   wherein the tampon applicator assembly has a length and an insertion tip region adjacent a barrel region, wherein the tampon applicator has variable translucency in the insertion tip region.

9. The tampon applicator according to claim 8, wherein the insertion tip region decreases in translucency as it approaches the barrel region.

10. The tampon applicator assembly according to claim 8, wherein the tampon applicator assembly further comprises a plunger.

11. The tampon applicator assembly according to claim 10, wherein the plunger comprises a first plunger segment and a second plunger segment, wherein at least one of the first plunger segment and the second plunger segment is substantially translucent or has variable translucency.

12. The tampon applicator assembly according to claim 11, wherein at least a portion of a tampon pledget is visible through the tampon applicator assembly.

* * * * *